(12) United States Patent
Patel et al.

(10) Patent No.: US 8,793,896 B2
(45) Date of Patent: Aug. 5, 2014

(54) DEVICE AND METHOD FOR CONTROLLING A DEHYDRATION OPERATION DURING A FREEZE-DRYING TREATMENT

(75) Inventors: Ketan Patel, Monroeville, PA (US); Didier Pierrejean, Groisy (FR); Cyrille Nomine, Epagny (FR); Aurélie Chapron, Annecy (FR)

(73) Assignee: Adixen Vacuum Products, Annecy (FR)

( * ) Notice: Subject to any disclaimer, the term of this patent is extended or adjusted under 35 U.S.C. 154(b) by 224 days.

(21) Appl. No.: 13/576,320

(22) PCT Filed: Feb. 1, 2011

(86) PCT No.: PCT/EP2011/051392
§ 371 (c)(1),
(2), (4) Date: Sep. 26, 2012

(87) PCT Pub. No.: WO2011/092344
PCT Pub. Date: Aug. 4, 2011

(65) Prior Publication Data
US 2013/0008048 A1  Jan. 10, 2013

(30) Foreign Application Priority Data
Feb. 1, 2010 (FR) .................................. 10 50686

(51) Int. Cl.
*F26B 5/06* (2006.01)
*G01N 21/68* (2006.01)

(52) U.S. Cl.
CPC . *F26B 5/06* (2013.01); *G01N 21/68* (2013.01)
USPC .......... 34/290; 34/298; 422/186.04; 204/164; 165/185; 62/116; 206/438

(58) Field of Classification Search
USPC .......... 34/284, 285, 286, 287, 289, 290, 291, 34/293, 297, 298; 422/186.04, 28; 204/164; 165/185, 195; 62/114, 115, 62/116; 206/438
See application file for complete search history.

(56) References Cited

U.S. PATENT DOCUMENTS 3,020,645 A * 2/1962 Copson ........................... 34/287
6,060,019 A * 5/2000 Spencer et al. ................. 422/23

(Continued)

FOREIGN PATENT DOCUMENTS

EP  1 022 559 A1  7/2000
EP  1 674 812 A1  6/2006

(Continued)

OTHER PUBLICATIONS

International Search Report of the ISA for PCT/EP2011/051392; Apr. 28, 2011.

*Primary Examiner* — Steve M Gravini
(74) *Attorney, Agent, or Firm* — Daly, Crowley, Mofford & Durkee, LLP

(57) ABSTRACT

A device for controlling the dehydration operation during a freeze-drying treatment comprises a freeze-drying chamber (1) connected to a vacuum line, and a gas analyzer, for analyzing the gases contained in the chamber. The gas analyzer comprises a gas ionization system (8) comprising a plasma source (13) in contact with the gases, which plasma source is combined with a generator (15) capable of generating a plasma from said gases, and a system for analyzing the ionized gases, comprising a radiation sensor (17) located close to the plasma generation zone and connected to an apparatus (18) for analyzing the change in the radiative spectrum emitted by the plasma. According to the invention, the device includes a means (16) for repeatedly turning the plasma source (13) on and off. The device may further include an optical port (25) placed between the gas ionization system (8) and the freeze-drying chamber (1). The method of controlling the dehydration operation during a freeze-drying operation comprises an alternation of phases during which the plasma source (13) is turned on and phases during which the plasma source (13) is turned off.

20 Claims, 3 Drawing Sheets

(56) References Cited

U.S. PATENT DOCUMENTS

Figure 1:
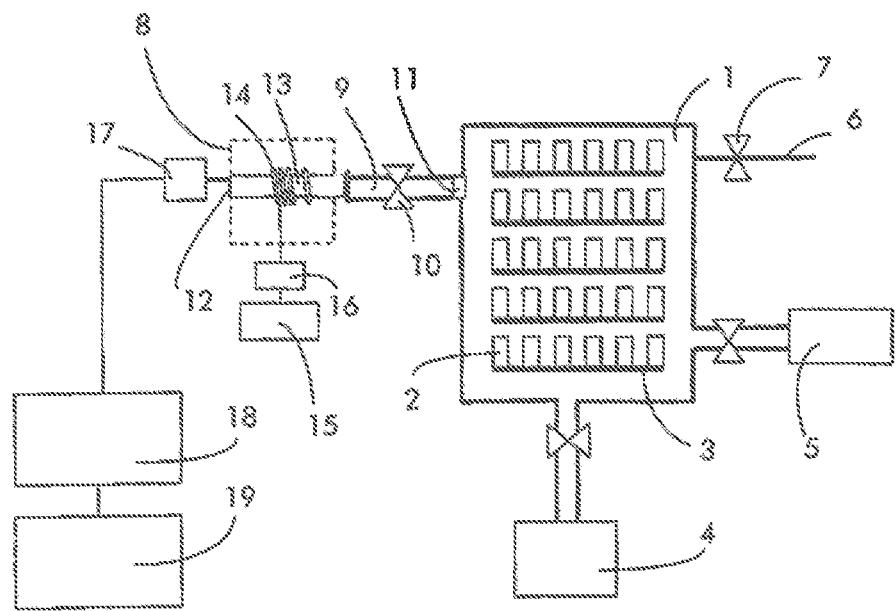

| | | | |
|---|---|---|---|
| 6,308,434 B1 * | 10/2001 | Chickering et al. | 34/373 |
| 6,643,014 B2 * | 11/2003 | Chevalier et al. | 356/316 |
| 6,649,019 B2 * | 11/2003 | Bernard et al. | 156/345.29 |
| 7,334,346 B2 * | 2/2008 | Nomine | 34/284 |
| 7,765,713 B2 * | 8/2010 | Ehrhard et al. | 34/89 |
| 8,371,039 B2 * | 2/2013 | Kuu et al. | 34/284 |
| 8,544,183 B2 * | 10/2013 | Kuu et al. | 34/92 |
| 2002/0153102 A1 * | 10/2002 | Bernard et al. | 156/345.29 |
| 2003/0037459 A1 * | 2/2003 | Chickering et al. | 34/576 |
| 2003/0116027 A1 * | 6/2003 | Brulls | 99/279 |
| 2004/0120869 A1 * | 6/2004 | Ko | 422/186.04 |
| 2006/0137212 A1 * | 6/2006 | Nomine | 34/284 |
| 2013/0008048 A1 * | 1/2013 | Patel et al. | 34/284 |

FOREIGN PATENT DOCUMENTS

| | | |
|---|---|---|
| EP | 1674812 A1 * | 6/2006 |
| WO | WO 02/23160 A1 | 3/2002 |
| WO | WO 2008/111701 A1 | 9/2008 |
| WO | WO 2009/021941 A1 | 2/2009 |

* cited by examiner

DEVICE AND METHOD FOR CONTROLLING A DEHYDRATION OPERATION DURING A FREEZE-DRYING TREATMENT

CROSS REFERENCE TO RELATED APPLICATIONS

This application is a National Stage application of PCT/EP2011/051392 filed on Feb. 1, 2011 and published in the French language, and entitled "DEVICE AND METHOD FOR CONTROLLING A DEHYDRATION OPERATION DURING A FREEZE-DRYING TREATMENT" which maims priority to French application FR1050686 filed on Feb. 1, 2010.

The present invention relates to tracking and monitoring the dehydration of substrates during a vacuum drying process, and more particularly to detecting the end of sublimation of water contained in substrates subjected to a freeze-drying treatment.

Freeze drying is a low-temperature process that consists in eliminating by sublimation the greater part of the water contained in a substrate. The foodstuffs industry, the pharmaceuticals industry (vaccines, serum, drugs) and bio-industries (yeasts) are those to which this process is most relevant, this process enabling them to obtain a long shelf life of an active principle (having a biological and/or medication activity) in a product that will be stored at a temperature close to room temperature. It is essential to track the kinetics of dehydration during freeze drying in order to control manufacturing costs but also to obtain a freeze-dried substrate of high quality.

The freeze-drying process includes two successive operations; freezing and dehydration. The dehydration operation includes two steps corresponding to two distinct physical phenomena; on the one hand fast sublimation in a vacuum of ice crystals that are formed during freezing, usually referred to as "primary desiccation", and on the other hand final desorption of unfrozen water, usually called "secondary desiccation".

The document EP-1 674 812, hereby incorporated by way of reference, proposes a device and a method for precisely determining the end of the primary desiccation step under conditions compatible with high aseptic requirements. The device described enables tracking of the species present in a freeze-drying enclosure by analyzing the evolution of their characteristic lines in the optical spectrum of the light emitted, by the plasma of the excited species. Active species, capable of destroying microorganisms quickly, are created when the plasma source is turned on. The plasma source is placed in an ionization chamber communicating with the freeze-drying enclosure. Gases contained in the enclosure are drawn into the ionization chamber, which is in contact with the interior of the freeze-drying enclosure containing the substrates to foe dehydrated.

However, deactivation of substrates submitted to freeze-drying treatment is observed. This deactivation is observed in particular with some types of pharmaceutical substrates such as vitamin C, saccharose, certain enzymes (dehydrogenase glutamate, dehydrogenase lactate, dehydrogenase malate), etc. The reduced catalytic capacity of the substrate once dehydrated is linked to a degraded enzyme structure leading to a reduction of the reaction rate. This loss of activity minimizes the efficacy of the substrate and reduces the quality of the substrate vis à vis its end use. In a pharmaceutical substrate, the active principle concentration is very low, the remainder being an additive. Consequently, this deactivation of the substrate impacts strongly on the activity of the drug when used by a patient.

An object of the present invention is to propose a device for controlling the dehydration operation during a freeze-drying treatment that is free of the drawbacks of the prior art. In particular, the invention proposes a control device enabling the activity of the substrates to be preserved following dehydration.

Another object of the invention is to propose a method of controlling the dehydration operation during a freeze-drying treatment that, by minimizing deactivation, yields substrates that have retained the greater part of their activity.

The present invention consists in a device for controlling the dehydration operation during a freeze-drying treatment, including:
- a freeze-drying enclosure connected to a vacuum line, and
- an analyzer of the gases contained in the enclosure, the gas analyzer comprising:
  - a gas ionization system comprising a plasma source in contact with the gases, combined with a generator adapted to generate a plasma from said gases, and
  - a system for analysis of the ionized gases comprising a radiation sensor situated in the vicinity of the area of generation of the plasma, connected to apparatus for analysis of the evolution of the radiation spectrum emitted by the plasma.

According to the invention, the gas analyzer further includes means for repetitively turning the plasma on and off.

According to one or more features of the dehydration operation control device, separately or in combination:
- the repetitive turning on and off means is adapted to turn the generator on or off;
- the repetitive turning on and off means is adapted to modify the flow rate or the pressure of the gases from which the plasma is generated;
- an optical gate is disposed between the gas ionization system and the freeze-drying enclosure;
- the optical gate is a metal part that is inserted into a quick connect;
- the plasma source is produced by inductive coupling.

The moisture (water vapor) molecules given off during the freeze-drying process and ionised by the plasma source generate oxidizing free radicals. Some of these oxidizing free radicals are liable to enter the freeze-drying enclosure and to react with the substrates to be dehydrated, degrading their structure and reducing their activity. Because of the continuous creation of oxidizing free radicals over a long period of time, their concentration in the enclosure is very high, which is favorable to their coming into contact with the pharmaceutical substrate. When the oxidizing free radicals come into contact with the pharmaceutical substrate, they are capable of reacting chemically with the pharmaceutical substrate, leading to its oxidation and deactivation.

Thus the invention has the advantage of limiting the formation of oxidizing free radicals by reducing the time period for which the plasma is turned on. Moreover, the presence of the optical gate prevents most of the oxidizing free radicals that are nevertheless formed from coming into contact with the pharmaceutical substrate to be dehydrated.

The invention also proposes a method of controlling the dehydration operation during a freeze-drying treatment in an enclosure during which the gases present in said enclosure are analysed by means of a gas ionization system comprising a plasma source.

According to the invention the method includes an alternation of phases during which the plasma is turned on and during which the plasma is turned off.

According to one or more features of the dehydration operation control method, separately or in combination:

the phases during which the plasma is turned on and the phases during which the plasma is turned off are in periodic succession;

the duration of a phase during which the plasma is turned off is from 2 minutes to 40 minutes;

the duration for which the plasma is turned on is from 1 second to 60 seconds;

the turned on duration is from 5 seconds to 30 seconds;

the plasma is turned on and off manually, turning the plasma on or off is controlled by a monitoring device of a radio-frequency generator of the plasma source.

The invention therefore has the advantage of minimizing the concentration of oxidising free radicals in the freeze-drying enclosure and thus of limiting deactivation of the substrates to be dehydrated.

Figure 2:
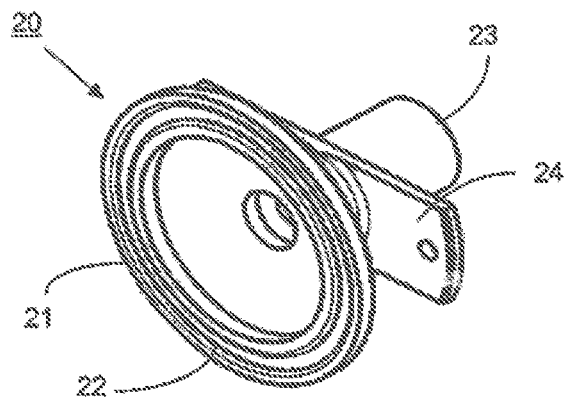
Figure 3:
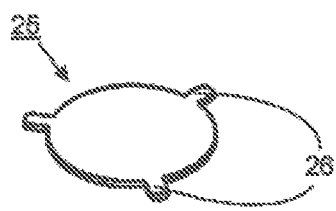
Figure 4:
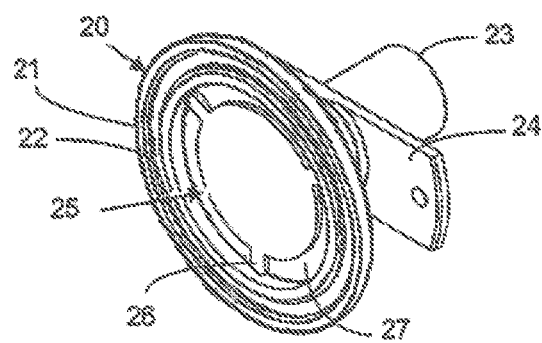
Figure 5:
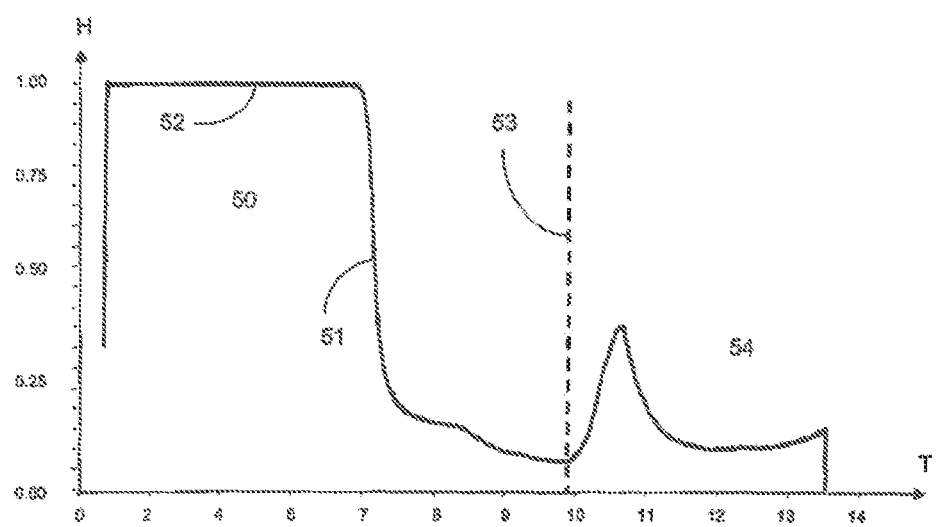

Other features and advantages of the present invention will become apparent on reading the following description of one embodiment, given by way of illustrative and nonlimiting example, of course, and from the appended drawings, in which:

FIG. 1 represents an installation for the treatment of substrates by freeze drying employing the invention, FIG. 2 is a perspective view of one example of a quick connect for establishing communication between a freeze-drying enclosure and a gas ionization system in one embodiment of the invention, FIG. 3 is a perspective view of an optical gate of one embodiment of the invention, FIG. 4 is a perspective view of the optical gate from FIG. 3 cooperating with the connect from FIG. 2, FIG. 5 shows the evolution of the moisture content of the substrates measured by the gas analyzer during the dehydration operation; the moisture content H in arbitrary units (0=no water vapor; 1=saturated with waiter vapor) is plotted on the ordinate axis and time T in hours on the abscissa axis.

In the embodiment of the invention shown in FIG. 1, the installation includes a vacuum enclosure 1 ($5 \cdot 10^{-3}$ to 3 mbar) containing the substrates 2 to be dehydrated and in which the freeze-drying treatment, is carried out. The enclosure 1 includes a heat source 3, integrated into stacked plates, for example, and is connected to a water vapor recovery trap 4, a primary vacuum pump 5, and a nitrogen supply pipe 6 fitted with a regulator valve 7.

The installation also includes a gas analyser comprising a gas ionization system 8 connected to the upper part of the enclosure 1 by a quartz tube 9 carrying a valve 10 and the open end of which communicates directly with the interior of the enclosure 1 via a stainless (ISO 2852) steel quick connect 11. The closed end 12 of the tube 9 is in quartz, optical glass or sapphire, and preferably in the form of an aspherical lens enabling efficient light collection. All the parts 8, 9, 10, 11, 12 of the gas analyzer that are in direct contact with the freeze-drying enclosure 1 are sterilized by SIP (Sterilization In Place) cycles.

In the gas ionization system 8, a plasma is generated inside the vacuum (<3 mbar) tube 9 in an area situated at the level of an induction coil 14, or excitation antenna, wound on the outside of the tube 9, this area forming an ionization chamber. The ionization chamber and the coil 14 that surrounds it constitute a plasma source 13. The induction coil 14 is energized by a 440 MHz 4 W ICP RF type radio-frequency generator 15 associated with repetitive on/off switching means 16 enabling the plasma source to be turned off and then turned on repeatedly. Light emitted by the plasma is detected, at the closed end 12 of the tube 9 by a sensor 17, which may notably be an optical fiber. This light is then conducted, for example by an optical fiber, to an optical emission spectrometer 18 to be analysed therein. Information may be stored and processed by means of a computer 19 connected to the optical emission spectrometer 18. The emitted light is characteristic of the substances present in the plasma and thus present inside the freeze-drying enclosure 1. In the present instance, lines characteristic of hydrogen (656 nm for example) and nitrogen (337 nm for example) are tracked during the dehydration operation. Information is stored and processed by the computer 19.

Most of the water molecules coming from a moist substrate, notably a pharmaceutical substrate, that are released during the freeze-drying process cross the freeze-drying enclosure 1 and are pumped by the primary vacuum pump 5. A condensation area may possibly be provided in the pipe connecting the freeze-drying enclosure 1 to the vacuum pump 5 in order to provide a surface for solidifying the water vapor and preventing it from reaching the vacuum pump 5, which could degrade the performance of the vacuum pump 5. The temperature of the condensation area is generally less than −50° C.

Some of the water molecules are directed to the gas analyser. They are excited by the energy coming from the radio-frequency generator 15 and emit light known as a "plasma". Upon de-excitation, the water molecules produce light and oxidising free radicals liable to produce a chemical reaction of oxidation with the pharmaceutical substrates 2 to be dehydrated, which are very sensitive to it.

In one embodiment of the invention, the repetitive on/off switching means 16 is adapted to enable a plasma to be generated in so-called "discontinuous" mode, which means that phases during which, the plasma source is turned, on and phases during which the plasma source is turned, off follow on in succession. In this discontinuous operating mode the plasma source is turned on for approximately 5 to 30 seconds every 2 to 40 minutes. The duration of the on phases and the off phases may be modified, as a function of the sensitivity of the pharmaceutical substrate 2 to be dehydrated. This reduces the total time period for which the plasma source is turned on. Because of this the quantity of oxidising free radicals formed is also reduced, minimising the effect, of oxidation of the substrate 2 to be dehydrated. In one particular embodiment the plasma source may be turned on and off manually. In another embodiment a monitoring device, for example a software, is adapted to control the repetitive on/off switching means by adapting the duration of the on and off phases of the plasma source. In a further embodiment, the repetitive on/off switching means 16 is adapted to modify the flow rate or the pressure of the gases from which the plasma is generated. For example, the repetitive on/off switching means 16 includes neutral gas injection means for modifying the flow rate of the gases. For example, with a plasma turned on, the flow rate of the gases is controlled so as to increase it until the plasma is turned off. In another example, the repetitive on/off switching means 16 includes means for controlling the opening of the valve 10 upstream of the plasma source 13 to modify the pressure of the gases. The repetitive on/off switching means 16 adapted to modify the flow rate or the pressure of the gases has the advantage of being simple to implement and of relatively low cost.

There has been represented in FIG. 2 an example of a two-way stainless steel quick connect 20, for example an ISO-KF 25 type quick connect or that sold under the trademark "TRICLAMP®" by the company "QUALITY CONTROLS". The connect 20 includes an inlet 21 provided with a fluorinated elastomer seal 22 designed to establish communication with the freeze-drying enclosure and an outlet 23 adapted to be connected to the open end of the tube leading to the gas ionization system. A fixing part 24 enables fastening of the connect 20 to the freeze-drying enclosure.

According to the invention, an optical gate 25 is mounted on the connect 20, by means of three fixing lugs 26, for example, as shown in FIG. 3. On the one hand the optical gate 25 enables blocking of the oxidizing free radicals to prevent them from entering the freeze-drying enclosure 1. On the other hand the optical gate 25 enables blocking of light radiation from the plasma liable to generate oxidizing free radicals inside the freeze-drying enclosure 1 itself. The optical gate 25 is for example a metal part, the shape of which is adapted to the shape of the inlet 21 of the quick connect 20.

According to the invention, the optical gate 25 is disposed at the inlet 21 of the connect 20 connected to the freeze-drying enclosure 1, as shown in FIG. 4. The optical gate 25 is inserted in the inlet 21 of the connect so as not to interfere with the sealed connection created by the seal 22 between the connect 20 and the freeze-drying enclosure 1. The aperture of the optical gate 25 is represented by the space 27 between the external edge of the gate 25 and the inside diameter of the inlet 21 of the quick connect 20. The opening of the optical gate 25 varies as a function of the accuracy of the moisture content measurement and the oxidation reaction.

Freeze drying a substrate begins with an operation of freezing the substrate. Water contained in the substrate is then cooled to a temperature lower than its triple point, the lowest temperature at which the solid and liquid phases are able to coexist. The freezing point, is from −50° C. to −80° C. The freezing operation is very critical because the substrate may be degraded if this operation is not carried out correctly. Once the freezing operation has been completed, either outside or inside the freeze-drying enclosure 1, the substrates 2 are subjected to the dehydration operation, which is represented diagrammatically in FIG. 5. Sublimation of water contained in the substrate is effected by input of heat, by conduction or radiation, by means of the heat source 3. Melting is prevented by maintaining the temperature in the enclosure below the triple point. The water vapor formed, is then recovered by means of the trap 4.

When the dehydration operation begins, the primary vacuum pump 5 is started and the pressure fails inside the freeze-drying enclosure 1. The pumping of the gases contained inside the freeze-drying enclosure 1 by the primary vacuum pump 5 firstly has the object of enabling the total pressure inside the enclosure 1 to be reduced. Thereafter pumping aims to maintain the pressure inside the enclosure 1 at low values compatible with the conditions necessary for sublimation, and to do so throughout the dehydration operation.

During the primary desiccation step 50, the pressure is reduced (by an amount of the order of a few millibar) and sufficient heat is supplied to the substrate to sublimate approximately 95% of the water that it contains. The quantity of heat necessary may be calculated using the latent heat of sublimation of water molecules. The primary desiccation step 50 is slow, for example several days in the case of an industrial-scale process, because if too ranch heat is applied quickly the structure of the substrate could be modified. During this step the pressure in the freeze-drying enclosure 1 is controlled by the imposition of a partial vacuum. The low pressure in the freeze-drying enclosure 1 is stabilized by the regulator valve 7 on the nitrogen feed pipe 6 connected to the freeze-drying enclosure 1. When the pressure fails because of the sublimation slowing down (period 51), the valve 7 is opened to inject more nitrogen into the freeze-drying enclosure 1. During the period 52 in which there is a great deal of sublimation of water little nitrogen is injected. The dehydration operation proceeds in a vacuum generally from 0.005 mbar to 0.5 mbar. A source of a cold plasma produced by inductive coupling (Inductive Coupled Plasma—ICP) is therefore highly-suitable since its operating pressure range is from 0.005 mbar to 10 mbar. The primary desiccation step 50 ends when all water present in the form of ice has been eliminated (point 53).

The secondary desiccation step 54 aims to eliminate unfrozen water molecules, those present in the form of ice having been eliminated during the primary desiccation step 51. This step of the freeze-drying process is governed by the absorption isotherms of the substrate. In this secondary desiccation step 54 the temperature is higher than in the primary desiccation step 51 and may even exceed 0° C., in order to break up any physico-chemical interaction that has occurred between the water molecules and the frozen substrate 2. The pressure is also usually lowered at this stage to encourage desorption (typically in the microbar range, or fractions of a Pascal). However, there are some substrates for which an increased pressure is more favorable.

At the end of the freeze-drying process, the final concentration of residual water in the substrate is extremely low and represents approximately 1% to 4% of its weight. After the end of the freeze-drying process the vacuum is generally broken with an inert gas such as nitrogen before the substrate is hermetically packaged.

A trial has been conducted in order to evaluate the advantages of the invention in terms of oxidation of pharmaceutical substrates subjected to freeze drying.

In the present case, enzyme activity was measured after a freeze-drying treatment carried out in the presence and in the absence of the repetitive on/off switching means 16. For this trial, the plasma was turned on for 30 seconds every 10 minutes. Activity was expressed as a percentage of the initial activity of the enzyme before freeze drying. To enable comparison between initial and final activity the result was referred to the specific activity, i.e. the activity per mg of substrate. The result obtained takes account of all dilutions necessary for effecting the measurements of activity using a spectrophotometer. Furthermore, for the measurement of activity after freeze-drying the freeze-dried enzymes were rehydrated to obtain the same volume as before the freeze-drying treatment.

A first series of measurements of the activity of the substrates was effected before and after a freeze-drying treatment of the substrates using no control device. The measurements were effected on substrates placed on plates at the top, in the middle and at the bottom of the enclosure 1. This series constitutes the series of measurements A.

A second series of measurements of the activity of the substrates was effected before and after a substrate freeze-drying treatment using a control device including no repetitive on/off switching means 16 and no optical gate 25. This second series constitutes the series of measurements B.

A third series of measurements of the activity of the substrates was effected before and after a substrate freeze-drying treatment using a control device including means 16 for repetitively switching the plasma source on and off enabling discontinuous operation of the plasma source. This third series constitutes the series of measurements D.

A fourth series of measurements of the activity of the substrates was effected before and after a substrate freeze-drying treatment using a control device including means 16 for repetitively switching the plasma source on and off and an optical gate 25. This fourth series constitutes the series of measurements D.

A first part of the trial related to the biological activity still present in the pharmaceutical substrate after being subjected to the freeze-drying treatment. The remaining activity of the substrate, expressed as a %, was calculated for each series of measurements from the formula:

$$\frac{\text{Activity after freeze drying}}{\text{Activity before freeze drying}} \times 100$$

The results given in table 1 are a comparison of the remaining activity for the series of measurements A and B as defined above,

TABLE 1

|  | A | B |
|---|---|---|
| Top | 90.10 | 38.90 |
| Middle | 91.10 | 50.80 |
| Bottom | 87.70 | 43.30 |

Analysis of the results from table 1 shows that the remaining activity in a substrate after a freeze-drying treatment was much lower if the freeze-drying treatment was carried out in the presence of a control device including no repetitive on/off switching means and no optical gate (series B). This may be interpreted as the control device generating oxidizing free radicals that affect the properties of the substrate submitted to a freeze-drying treatment.

It is seen further that the loss of biological activity of the treated enzymes is independent of the location of these substrates inside the freeze-drying enclosure. In other words, the position of the control device relative to the location of the substrates in the enclosure has no influence on the intensity of the oxidation of the pharmaceutical substrates.

The comparative results of the series of measurements A and B from table 1 show that the position of the substrate in the enclosure has no significant impact on the remaining activity, so the other series of measurements C and D were effected only on substrates placed, in the middle of the enclosure.

The results given in table 2 are a comparison of the remaining activity for the series of measurements A and C as defined above,

TABLE 2

|  | A | C |
|---|---|---|
| Middle | 97.10 | 92.20 |

Analysis of the results from table 2 shows that the remaining activity for the series C is considerably greater than for the series B. The biological activity of the freeze-dried pharmaceutical substrates is thus better preserved in the situation where a control device is used including repetitive on/off switching means enabling discontinuous operation of the plasma source.

In conclusion, the activity present in the substrates after a freeze-drying treatment when the treatment was effected using a control device including means for repetitively switching the plasma source on and off (series C) is very close to the remaining activity after a freeze-drying treatment when the treatment was effected, without using the control device (series A).

The results given in table 3 are a comparison of the remaining activity for the series of measurements A and D as defined above.

TABLE 3

|  | A | D |
|---|---|---|
| Middle | 97.10 | 95.99 |

Analysis of the results from table 3 shows that the remaining activity for the series D is improved by the presence of an optical gate. In this situation the optical gate thus exercised the function of a shield preventing oxidising free radicals from entering the freeze-drying enclosure.

In conclusion, the activity present in the substrates after a freeze-drying treatment is hardly any lower than the initial activity when the treatment was effected using a control device including means for repetitively switching the plasma source on and off and an optical gate (series D). It is further seen that the remaining activity in this situation is of the same order as the remaining activity when the treatment was effected with no control device used (series A).

A second part of the study related to the level of oxidation measured on pharmaceutical substrates after a freeze-drying treatment.

Table 4 gives the rates of oxidation, expressed as a %, for the series of measurements A to D as defined above,

TABLE 4

|  | A | B | C | D |
|---|---|---|---|---|
| Middle | 1.00 | 5.80 | 1.70 | 1.00 |

Analysis of the results from table 4 confirms the conclusions drawn from, the first part of the trial.

Analysis of the results from table 4 shows that the rate of oxidation of the pharmaceutical substrates was considerable lower when the freeze-drying treatment was carried out in the presence of a control device including means for repetitively turning the plasma source on and off enabling discontinuous operation (series of measurements C), and is close to the rate of oxidation observed in the absence of a control device (series of measurements A).

In the case of the series of measurements D in which the freeze-drying treatment was carried out in the presence of a control device including repetitive on/off switching means and an optical gate, enabling blocking of access to the freeze-drying enclosure by oxidizing free radicals, the rate of oxidation is even lower and of the same order as the rate of oxidation observed in the absence of any control device (series of measurements A).

The invention claimed is:

1. A device for controlling a dehydration operation during a freeze-drying treatment, the device including:
   a freeze-drying enclosure connected to a vacuum line, and
   a gas analyzer adapted to analyze gas contained in said freeze-drying enclosure, said gas analyzer comprising:
   a gas ionization system comprising:
      a plasma source in contact with gas contained in said freeze-drying enclosure; and
      a radio-frequency generator coupled to said plasma source, said plasma source and radio-frequency generator operable to generate a plasma from gas contained in said freeze-drying enclosure; and a system for analysis of ionized gases, said system comprising:

a radiation sensor situated in the vicinity of the area of generation of the plasma; and apparatus for analysis of the evolution of the radiation spectrum emitted by the plasma, said apparatus coupled to said radiation sensor characterized in that it includes means for repetitively turning the plasma source on and off.

2. The device claimed in claim 1, wherein said means for repetitively turning said plasma source on and off is adapted to turn the radio-frequency generator on and/or off.

3. The device claimed in claim 1, wherein said means for repetitively turning said plasma source on and off is adapted to modify the flow rate or the pressure of the gases from which the plasma is generated.

4. The device claimed in claim 1, further comprising an optical gate disposed between the gas ionization system and the freeze-drying enclosure.

5. The device claimed in claim 4, wherein the optical gate is a metal part that is inserted into a quick connect.

6. The device claimed in claim 1, wherein said plasma source is produced by inductive coupling.

7. A method of controlling a dehydration operation during a freeze-drying treatment in an enclosure during which the gases present in said enclosure are analyzed by means of a gas ionization system comprising a plasma source, characterized in that it includes an alternation of phases during which the plasma is turned on and during which the plasma is turned off.

8. The method claimed in claim 7, wherein the phases during which the plasma is turned on and the phases during which the plasma is turned off are in periodic succession.

9. The method claimed in claim 7, wherein the duration of a phase during which the plasma is turned off is from 2 minutes to 40 minutes.

10. The method claimed in claim 7, wherein the duration of a phase during which the plasma is turned on is from 1 second to 60 seconds.

11. The method claimed in claim 10, wherein the duration of a phase during which the plasma is turned on is from 5 seconds to 30 seconds.

12. The method claimed in claim 7, wherein turning the plasma on or off is controlled by a monitoring device of a radio-frequency generator of the plasma source.

13. A device comprising:
a freeze-drying enclosure;
a vacuum line coupled to said freeze-drying enclosure; and
a gas analyzer adapted to analyze gas contained in said freeze-drying enclosure, said gas analyzer comprising:
a gas ionization system comprising:
a plasma source in fluid communication with said freeze-drying enclosure through said vacuum line, said plasma source for generating plasma; and
a radio-frequency generator coupled to said plasma source, said plasma source and radio-frequency generator operable to generate a plasma from gas contained in said freeze-drying enclosure; and
a system for analyzing ionized gases, said system comprising:
a radiation sensor disposed proximate said plasma source; and
apparatus for analysis of evolution of a radiation spectrum emitted by a plasma, said apparatus coupled to said radiation sensor and comprising means for repetitively turning said plasma source on and off.

14. The device claimed in claim 13, wherein said means for repetitively turning said plasma source on and off comprises means for turning said radio-frequency generator on and/or off.

15. The device claimed in claim 13, wherein said means for repetitively turning said plasma source on and off is adapted to modify a flow rate and/or a pressure of gases from which the plasma is generated.

16. The device claimed in claim 13, further comprising an optical gate disposed between said gas ionization system and said freeze-drying enclosure.

17. The device claimed in claim 16, wherein said optical gate comprises a metal part inserted into a quick connect.

18. The device claimed in claim 13, wherein said plasma source is provided by an induction coil disposed around a portion of said quartz tube to form an ionization chamber and wherein said ionization chamber and the coil that surrounds it comprise a said plasma source.

19. The device claimed in claim 13 wherein:
said vacuum line is provided as a tube having a first end coupled to said freeze-drying enclosure and a second dosed end; and
said radiation sensor disposed at the dosed end of said tube to detect light emitted by the plasma.

20. The device claimed in claim 13 wherein the dosed end of said tube is provided as a lens.

* * * * *